United States Patent [19]

Ramstad et al.

[11] 4,042,499
[45] Aug. 16, 1977

[54] LIQUID ADSORPTION CHROMATOGRAPHIC APPARATUS AND METHOD

[75] Inventors: Tore Ramstad; Nels H. Mahle; Ralph Matalon, all of Midland, Mich.

[73] Assignee: The Dow Chemical Company, Midland, Mich.

[21] Appl. No.: 710,986

[22] Filed: Aug. 2, 1976

[51] Int. Cl.² ............................................ H01D 15/08
[52] U.S. Cl. ................................ 210/31 C; 210/198 C
[58] Field of Search .......................... 210/31 C, 198 C; 73/61.1 C

[56] References Cited

U.S. PATENT DOCUMENTS

| | | | |
|---|---|---|---|
| 3,701,609 | 10/1977 | Bailey | 210/198 C |
| 3,725,260 | 4/1973 | Stalling et al. | 210/31 C |
| 3,846,297 | 11/1974 | Thaw | 210/31 C |
| 3,926,559 | 12/1975 | Stevens | 210/31 C |
| 3,963,614 | 6/1976 | Ozawa | 210/198 C |

Primary Examiner—John Adee
Attorney, Agent, or Firm—J. M. Kuszaj

[57] ABSTRACT

Apparatus and method for the repetitive use of a single packed chromatographic column for the separation of a first solute from at least one second solute of differing polarity, said solutes being commingled in a sample solution. The sample solution is introduced into the inlet end of a single re-usable chromatographic column packed with a charge of porous adsorbent material suited to preferentially adsorb the first solute. A series of different eluants are then passed through the stationary phase to selectively stepwise elute the second solute, and the first adsorbed solute, and to regenerate the stationary phase before introduction of a subsequent sample solution into the column. A control means coordinates the respective sequential processing of each of a plurality of sample solutions through the same charge of porous adsorbent material in the column.

19 Claims, 1 Drawing Figure

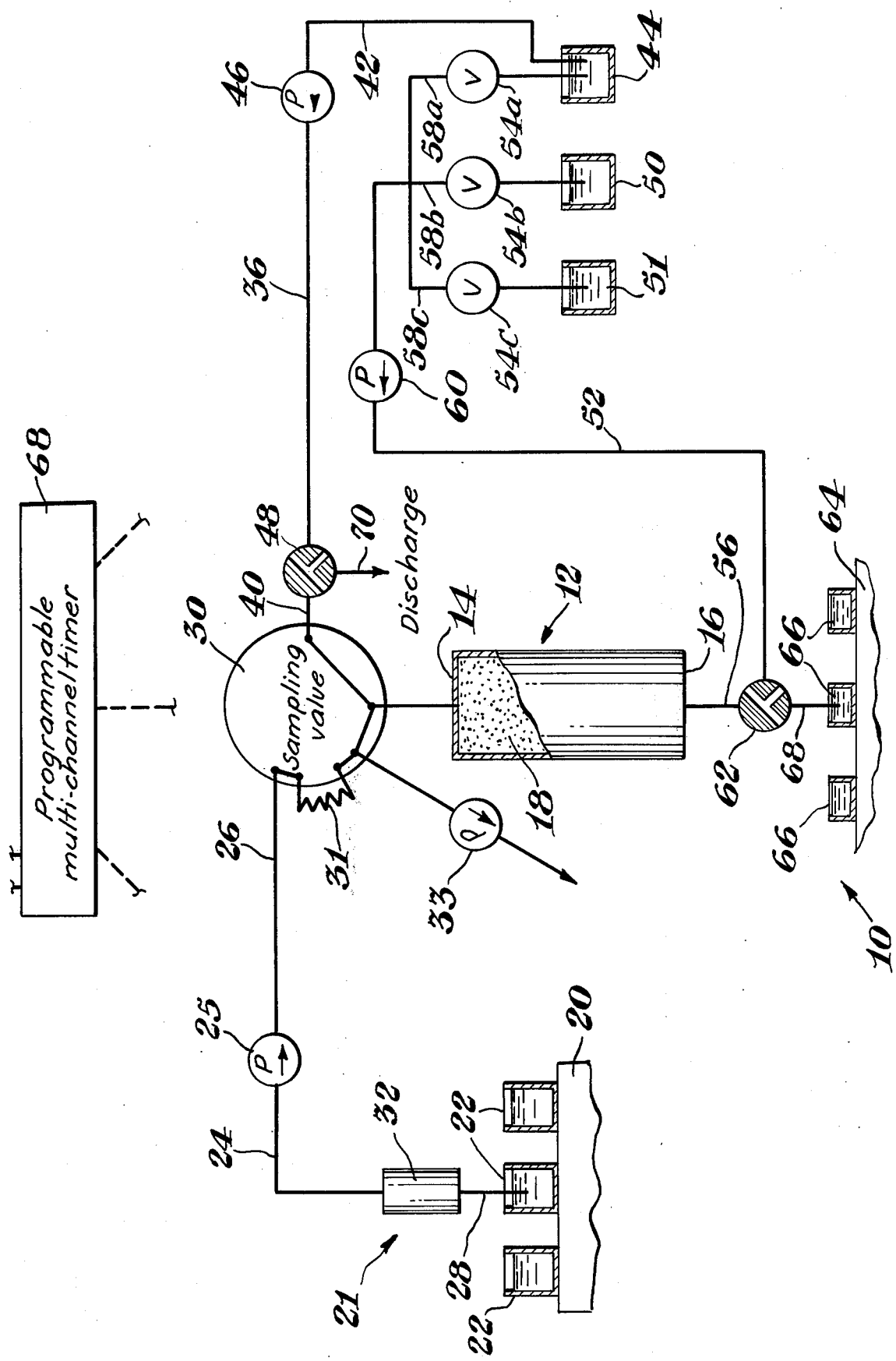

LIQUID ADSORPTION CHROMATOGRAPHIC APPARATUS AND METHOD

FIELD AND BACKGROUND OF THE INVENTION

This invention relates to an apparatus and a method for chromatographic separation. More in particular, it relates to an improved process and apparatus for the separation of polar species by liquid adsorption chromatography with a re-usable column packing.

Chemical separation of species of differing polarity by column adsorption chromatography has become a widely used technique, for example, in the area of pesticide residue analysis. The common procedure has been to pass a solution containing the species to be separated through a column containing a porous adsorbent material such as silica gel to preferentially adsorb one of the species. In order to re-use the adsorption column for additional separations, the adsorbed species are manually removed from the column, and the column or at least its packing discarded. A typical method is shown in an article by W. B. Crummett and R. H. Stehl in *Environmental Health Perspectives*, September 1973, pp. 15-25.

The manual techniques are inefficient and impractically slow, and are thus unacceptable for commercial applications. Furthermore, such techniques are more likely to cause exposure to the typical pesticides separated by these methods which can be highly toxic to humans. It is therefore desired to develop a new and automated process for repetitive use of a single charge of particulate porous adsorbent material in a liquid adsorption column for the separation of species of differing polarity commingled in solution.

SUMMARY OF THE INVENTION

A liquid adsorption chromatographic apparatus for the repetitive use of a single packed chromatographic column for the separation of a first solute from at least one second solute of differing polarity, said solutes being commingled in a sample solution, has been discovered. The apparatus comprises: a chromatographic column with an inlet and an outlet end; sample supply means, in fluid communication with the inlet end, for passing sample solution into the column; respective reservoirs for a first and second eluant and a stripping fluid; a first eluant supply means, communicating with both the inlet end of the column and the reservoir for the first eluant, for passing the first eluant into the column at the input end; a second eluant supply means for selectively passing each of the first eluant, the second eluant and the stripping fluid into the column at the output end, said means communicating with each respective reservoir and the outlet end of the column; discharging means, communicating with the column, for removing effluent from the column; and control means for coordinating the sequential operation of the means specified above.

The present apparatus is used in an improved chromatographic process for the separation of a first solute from at least one second solute of differing polarity, said solutes being commingled in a sample solution, by the preferential adsorption of the first solute on a chromatographic column with a solid particulate stationary phase consisting essentially of a charge of porous adsorbent material selected from the group consisting of silica gel, alumina and magnesium silicates. The improvement comprises sequentially: passing a first eluant through the stationary phase at a rate sufficient to selectively elute the second solute from the stationary phase; thereafter passing a second eluant through the stationary phase in a direction countercurrent to the direction of the first eluant to selectively elute the first absorbed solute from the stationary phase; thereafter passing a stripping fluid through the stationary phase in a direction cocurrent to the direction of the second eluant to remove second eluant retained on the stationary phase; and then passing additional first eluant through the stationary phase in a direction cocurrent to the direction of the stripping fluid to re-equilibrate the stationary phase for introduction of a subsequent sample solution into the column.

BRIEF DESCRIPTION OF THE DRAWING

The single FIG. shown in the drawing is a schematic representation of one embodiment of the apparatus of the present invention.

DESCRIPTION OF THE PREFERRED EMBODIMENT

Referring now to the drawing, there is depicted schematically an instrument in accordance with the present invention generally designated by the reference numeral 10. The instrument comprises a chromatographic column 12 with an inlet end 14 and an outlet end 16.

The column 12 is packed with a particulate stationary phase 18 which consists essentially of a charge of porous adsorbent material suited to preferentially adsorb the first solute. Preferably, the column 12 is packed with a particulate stationary phase 18 consisting essentially of a charge of porous inorganic adsorbent material containing at least one member selected from the group consisting of silica gel, alumina and magnesium silicates. More preferably, the column 12 is packed with a particulate stationary phase 18 consisting essentially of a charge of silica gel. Preferably, the charge of porous adsorbent material is chosen so that the most polar solute is preferentially adsorbed on the stationary phase.

Preferably, the charge of porous adsorbent material contains irregularly shaped particles of sufficient size to pass through a 100 mesh sieve (United States Sieve Series). More preferably, the porous material contains substantially spherical particles of sufficient size to pass through a 200 mesh sieve but be retained on a 400 mesh sieve. Most preferably, the porous adsorbent material contains substantially spherical particles of sufficient size to pass through a 400 mesh sieve.

A sample supply means, generally designated by the reference numeral 21, is located in a spaced relationship adjacent to the column 12, and is in fluid communication with the inlet end 14 of the column 12. The sample supply means 21 includes a sample conduit 24, with an inlet end 28 and an outlet end 26. The inlet end 28 of the sample conduit 24 communicates with at least one sample reservoir 22. The outlet end 26 of the sample conduit 24 communicates with a sampling valve 30.

The sampling valve 30 is in fluid communication with the input end 14 of the column 12, and is adapted to selectively pass a predetermined amount of a sample solution into the column 12. The sampling valve 30 is of a design well known in the art and includes a sample conduit loop 31 of predetermined volume in fluid communication with a pump 33 adapted to control the flow of sample solution through the sample conduit loop 31. A pump 25 is interposed in the sampe conduit 24 between the sample reservoir 22 and the sampling valve 30 and controls the flow of sample solution through the sample conduit 24 and into the sampling valve 30 at a predetermined rate. Preferably a plunger assembly 32 is fitted with a hypodermic needle and is operatively connected to the input end 28 of the sample conduit 24, for introducing sample solution into the conduit.

The sample supply means 21 also includes a conveying means 20 for supporting and intermittently moving at respective times each of a series of the sample reservoirs 22 into a predetermined position for withdrawing of sample solution into the sample conduit 24. Any suitable conveying means, such as a circular turntable or a conveyor or the like, may be used to support and move the series of sample reservoirs 22.

Reservoirs 44, 50 and 51 are provided for a first eluant, a second eluant, and a stripping fluid, respectively. An inlet end 42 for a first eluant conduit 36 communicates with the reservoir 44 for the first eluant, and an outlet end 40 of the first eluant conduit 36 communicates with the sampling valve 30. Sampling valve 30 is adapted to selectively communicate with the input end 14 of column 12. A pump 76 is interposed in the first eluant conduit 36 between the reservoir 44 for the first eluant and the sampling valve 30. The pump 46 is adapted to control the flow of first eluant through the first eluant conduit 36 and to the sampling valve 30 at a predetermined rate. A first flow control means 48 is interposed in the first eluant conduit 36 between the sampling valve 30 and the pump 46. The first flow control means 48 is adapted to select a fluid passing between the first eluant conduit 36 and the sampling valve 30.

The first flow control means 48 is also adapted to select a fluid passage between the sampling valve 30 and a waste discharging means. When the first flow control means 48 is in discharge position, effluent such as second eluant, first solute, stripping fluid and first eluant can be selectively removed from column 12 by flowing through a fluid passage from the input end 14 through the sampling valve 30 and out the discharge conduit 70 communicating with the first control means 48. This flow can be controlled by suitable means attached to the discharge conduit 70 such as a pump.

A second eluant conduit 52 is provided. An outlet end 56 of the second eluant conduit 52 communicates with the outlet end 16 of the column 12. A plurality of alternate inlet ends 58a, 58b, 58c of the second eluant conduit 52 communicate respectively with one each of the reservoirs 44, 50 and 51. A pump 60 is interposed in the second eluant conduit 52 between the reservoirs 44, 50, 51 and the outlet end 56 of the second eluant conduit 52. The pump 60 is adapted to control from time to time the flow of a selected one of the first eluant, the second eluant and the stripping fluid, through the second eluant conduit 52 at a predetermined rate. A plurality of control valves 54a, 54b, 54c interrupt the second eluant conduit 52 between the pump 60 and respectively each reservoir 44, 50 and 51. The control valves are adapted to selectively pass a first eluant, a second eluant, or a stripping fluid into the second eluant conduit 52. A second flow control means 62 is interposed in the second eluant conduit 52 between the column 12 and the pump 60. The second flow control means 62 is adapted to select a fluid passage between the second eluant conduit 52 and the column 12.

The second flow control means 62 is also adapted to select a fluid passage between the column 12, a collection conduit 68, and each of a series of collection reservoirs 66. Collection conveying means 64 is adapted to support and intermittently move at respective times each of the series of collection reservoirs 66 into a predetermined position for receiving solute eluted from the stationary phase 18. Preferably, conveying means 20 and collection conveying means 64 are identical, with sample reservoirs 22 occupying one track and collection reservoirs 66 occupying another track.

A control means 68 is provided for coordinating the sequential operation of the sample supply means, the first eluant supply means, the second eluant supply means, and the discharge means.

In the practice of the present process, a sample solution containing a commingling of a first solute with at least one second solute of differing polarity is moved from the sample reservoir 22 through the sample conduit 24 and introduced into the sampling valve 30. Generally only up to about 0.15 part per million (ppm) of second solute is commingled with only the first solute in the sample solution.

A controlled predetermined amount of the sample solution is then introduced into the sample conduit loop 31 and then into the first end 14 of the column 12. Generally, the weight of the sample solution introduced into the column is sufficient to produce a sample to adsorbent material weight ratio of from about 1 to 10 to about 1 to 15. For example, 1 gram of the sample solution can be introduced into a column containing 13 grams of silica gel.

A first eluant is moved from reservoir 44 through the first eluant conduit 36 and introduced into the sampling valve 30. The first eluant is then selectively passed through the stationary phase 18 at a rate sufficient to selectively elute the second solute from stationary phase 18. The second eluant is moved from reservoir 50 through second eluant conduit 52 and is passed through the stationary phase 18 in a direction countercurrent to the direction of first eluant to selectively elute the first adsorbed solute from the stationary phase 18. The stripping fluid is then moved from reservoir 51 through the second eluant conduit 52 and is passed through the stationary phase 18 in a direction cocurrent to the direction of the second eluant to remove any second eluant retained on the stationary phase 18 by the previous step. Finally, additional first eluant is moved from reservoir 44 through the second eluant conduit 52 and is passed through the stationary phase 18 in a direction cocurrent to the direction of the stripping fluid to substantially re-equilibrate the stationary phase 18 for introduction of a subsequent sample solution into column 12.

The eluants and the stripping fluid are of differing eluting power. The first eluant is the least polar, and the weakest eluant, with the polarity and eluting power increasing with the stripping fluid and the second eluant. Preferably, however, the first eluant is more polar than the second solute. Preferably, the first solute is more polar than the second solute.

The present method and apparatus are well adapted for the rapid and automatic separation of a great variety of species with differing polarities, especially where the species are neutral rather than inonic and have approximately the same molecular weight. Examples of the types of systems amenable to the present method can include highly toxic halogenated dioxin compounds contained in esters of 2,4,5-trichlorophenoxyacetic acid (2,4,5-T), benzo-pyrenes contained in oils and tars, other halogenated pesticides, such as dichlorodiphenyltrichloroethane (DDT) or dichlorodiphenyldichloroethylene (DDE) contained in their formulators, and the like.

The automated process of the present invention has been especially useful in separating and collecting trace levels of the highly toxic 2,3,7,8-tetrachlorodibenzo-p-dioxin (TCDD) from esters of 2,4,5-trichloro phenoxyacetic acid (2,4,5-T) in herbicide preparations. A single charge of porous adsorbent silica gel in the column has been used over 400 times to provide a rapid, accurate and safe chemical cleanup process for these species facilitating subsequent indentification and quantification.

The following examples serve to illustrate the use of the method and apparatus of the present invention. However, the scope of the invention is not intended to be limited thereto.

EXAMPLES

A 5 millimeter (mm) inside diameter stainless steel chromatographic column 1 meter in length, and having a single turn was packed dry with 100–200 mesh (U.S. Standard) "high purity" silica gel (Curtin Scientific).

A 5 gram (g) sample portion of the 1-isobutoxy-2-propyl ester (PiB) of 2,4,5-trichlorophenoxyacetic acid (2,4,5-T) containing trace amounts of the highly toxic 2,3,7,8-tetrachlorodibenzo-p-dioxin (TCDD) was weighed into a #7 dram vial and diluted to 25 milliliters (ml) with 1:4 (volume/volume) benzene-hexane. The vial was capped with aluminum foil, shiny side up, and placed on the inside track of a fraction collector reel (ISCO, Model 273).

A plunger fitted with a hypodermic needle, in combination with a Buchler peristaltic pump, withdrew the sample from the vial and introduced it into an automatic sampling valve (valco automatic valve-AVSV-6-HP) with a 5.0 ml external loop attached. Five milliliters of sample solution was then transferred from the sampling valve into the column.

After sample introduction, 20 milliliters of the 1:4 benzene-hexane was pumped into the input end of the column at a flow rate of 1 milliliter per minute. The 1:4 benzene-hexane solution passed downward through the silica gel in the column and selectively eluted the TCDD from the column while essentially retaining the more polar ester (PiB) on the top portion of the silica packing.

To remove the PiB ester from the silica packing 100 milliliters of a solution of tetrahydrofuran (THF) and benzene in a ratio of 15 parts by volume of THF to 85 parts by volume benzene was passed upward through the column in a direction reverse to that of the first solution at a flow rate of 4 milliliters per minute. Switching between the forward and reverse flow directions was accomplished with the aid of three-way valves located near the inlet and the outlet of the column.

Passage of the THF-benzene eluant through the column in a reverse direction was used to prevent the PiB ester from contacting the lower portion of the silica packing. This served two purposes: (1) the chance of coelution of components which may interfere in the determination of TCDD by gas chromatography - mass spectrometry was minimized; and (2) by sparing the lower portion of the silica packing from contacting the bulk of the sample solution, column life was extended. Our experiments show that the PiB ester was retained on the top third of a freshly packed silica column. As a final precaution to help extend column life, the THF was shaken with 5 A molecular sieves to minimize surface deactivation due to the introduction of moisture.

After the passage of the 15:85 THF-benzene, 110 milliliters of benzene were passed through the silica packing in a direction generally cocurrent with the direction of the 15:85 THF-benzene solution. The benzene solution was passed through the silica packing to remove any THF that may have been retained on the silica prior to the introduction of the next sample.

Following the passage of benzene through the silica packing, 55 milliliters of a fresh 1:4 benzene-hexane solution was passed through the silica packing in a direction cocurrent with the direction of the benzene to re-equilibrate the silica packing for the introduction of the next sample.

The entire sample system was under the control of a multichannel, mechanically-programmable timer (Sealectro, 092-286-5501-000). Each channel of the timer drum had 60 positions. In this system the drum was stepped once every 96 seconds by a 1/24 rpm synchronous motor (Sealectro, 095-026-6525-000) so that an entire cycle (one sample processed) took 96 minutes.

Extra sampling time was allotted for flushing out the viscous sample with solvent to prevent plugging of the sample line, and also to insure against cross-contamination from one sample to the next. The collected dioxin was also positioned under an air jet to evaporate the benzene-hexane solvent.

A protective feature in the apparatus was a simple start/stop circuit. A flip-flop (multivibrator) was interposed between a microswitch and a power relay, serving as a buffer in case of mechanical slippage of the shut-off assembly. The microswitch was closed by a pin located on the fraction collector reel when the timer reached position 59 after the last sample had been processed. After loading the next batch of samples, one needed only to press the clear button to restart the system.

A light emitting diode (LED) indicated when the samples where being processed. Proper circuitry layout, routing of lead-in wire, and circuit shielding prevented false triggering of digital circuitry. An additional protective feature was the inclusion of a pressure switch (Barksdale Valves, DIS-A80) which automatically shut off power to the system thus protecting the sample, in the event of a severe air leak.

The timer, the start/stop circuit, the air solenoids, and the terminal strips in the manifold for the pneumatic lines were all located in a control module. Because of the high flammability of each of the solvents, the solvent containers were 0.5 gallon (safety) cans with flame arresters. As a precaution against accumulation of flammable vapors in the event of a leak, points of sparking were purged with a light stream of air. Finally, since the collection of TCDD was concentrated under a current of air, all components other than the control module were located inside a fume hood.

The extracts obtained from the column were analyzed for TCDD as follows:

The concentration of TCDD was determined by gas chromatography-mass spectroscopy (GC-MS) using a LKB 9000S. Injections of 3–5 microliters were made onto a 3 foot by 3 millimeter glass column packed with 3 percent OV-3 on Gas Chrom Q. The analysis conditions were as follows:

Carrier gas:helium at 35 cubic centimeters per minute. (cc/min.).

Temperatures: Column—230° C;
Injector—250°C;
Separator—270°C;
Ion source—270°C.
Electron energy: 70 eV.
Acceleration voltage: 3.5 KV.
Trap current: 60 μA.

Ninety-six different sample solutions of PiB ester of 2,3,4-T were studied by the present method. The same PiB ester sample was run intermittently. The results are shown in Table I. The average TCDD content for these determinations was 0.026 part per million with a standard deviation of 0.002 part per million. Nine blanks containing no TCDD were interspersed among the samples; no TCDD was determined in the blanks with a detection limit of 0.005 part per million.

A number of the 96 sample solutions of the PiB ester were also studied by the manual method of Crummett and Stehl (W. B. Crummett and R. H. Stehl, *Environmental Health Perspectives*, Sept. 15, 1973). In addition, one each of the butoxylpropylene ester of 2,4,5-T and a PiB ester of 2-(2,4,5-trichlorophenoxyl) propionic acid (Silvex) were studied. The TCDD concentrations found are shown in Table II along with the corresponding sample number. The agreement between the automated and manual processes was excellent. There was no indication of column degradation.

Table I

| TCDD Concentration for the same Pib Ester of 2,4,5-T | | | |
|---|---|---|---|
| Sample No. | ppm TCDD | Sample No. | ppm TCDD |
| 21 | 0.026 | 50 | 0.025 |
| 24 | 0.028 | 51 | 0.024 |
| 25 | 0.030 | 52 | 0.025 |
| 27 | 0.024 | 53 | 0.026 |
| 29 | 0.026 | 55 | 0.025 |
| 31 | 0.026 | 57 | 0.024 |
| 33 | 0.029 | 59 | 0.024 |
| 34 | 0.028 | 60 | 0.025 |
| 35 | 0.034 | 61 | 0.024 |
| 36 | 0.028 | 62 | 0.024 |
| 37 | 0.026 | 63 | 0.025 |
| 38 | 0.028 | 64 | 0.026 |
| 39 | 0.026 | 65 | 0.024 |
| 41 | 0.026 | 67 | 0.025 |
| 43 | 0.026 | 72 | 0.023 |
| 44 | 0.023 | 73 | 0.026 |
| 48 | 0.024 | 79 | 0.024 |
| 49 | 0.026 | 90 | 0.024 |

Table II

| Correlations of Automated and Manual Cleanups | | | | |
|---|---|---|---|---|
| | | ppm 2,3,7,8-TCDD | | |
| Sample No. | Sample | Automated | Manual | Difference[1] |
| 40 | PiB Ester of 2,4,5-T | 0.017 | 0.014 | 0.003 |
| 42 | " | 0.030 | 0.029 | 0.001 |
| 45 | " | 0.020 | 0.021 | −0.001 |
| 46 | " | 0.032 | 0.032 | 0.000 |
| 47 | " | 0.027 | 0.027 | 0.000 |
| 68 | " | 0.028 | 0.029 | −0.001 |
| 69 | " | 0.023 | 0.023 | 0.000 |
| 75 | " | 0.028 | 0.029 | −0.001 |
| 76 | " | 0.030 | 0.029 | 0.001 |
| 77 | " | 0.056 | 0.056 | 0.000 |
| 80 | PiB Ester of Silvex | 0.036 | 0.034 | 0.002 |
| 81 | PiB Ester of 2,4,5-T | 0.050 | 0.049 | 0.001 |
| 82,91 | " | 0.092 | 0.091 | 0.001 |
| 83 | " | 0.020 | 0.022 | −0.002 |
| 84 | " | 0.048 | 0.050 | −0.002 |
| 85 | Butoxypropyl Ester of 2,4,5-T | 0.008 | 0.008 | 0.000 |
| 96 | PiB Ester of 2,4,5-T | 0.114 | 0.119 | −0.005 |

[1]Different = Automated - Manual

On carrying out the process described above with other solid particulate adsorbent material in the column such as aluminum, or magnesium silicates, similar excellent separations and repeated uses of the column material are achieved with the sample types described.

These examples clearly show the ability of the present invention to repeatedly use a single column of porous adsorbent material for automatic chemical cleanup. The system accuracy and reliability, as determined by checking against identical samples manually prepared, is excellent. The health hazards to humans is minimized.

What is claimed is:

1. In a liquid adsorption chromatographic process for the separation of a first solute from at least one second solute of differing polarity said solutes being commingled in a sample solution, by the preferential adsorption of the first solute on a chromatographic column with a solid particulate stationary phase consisting essentially of a charge of porous adsorbent material selected from the group consisting of silica gel, alumina and magnesium silicates, the improvement comprising sequentially:

a. passing a first eluant through the stationary phase at a rate sufficient to selectively elute the second solute from the stationary phase;

b. passing a second eluant through the stationary phase in a direction countercurrent to the direction of the first eluant to selectively elute the first adsorbed solute from the stationary phase;

c. passing a stripping fluid through the stationary phase in a direction cocurrent to the direction of the second eluant to remove second eluant retained on the stationary phase; and d. passing additional first eluant through the stationary phase in a direction cocurrent to the direction of the stripping fluid to re-equilibrate the stationary phase for introduction of a subsequent sample solution into the column.

2. The method of claim 1 wherein the first solute is an ester of 2,4,5 trichlorophenoxyacetic acid and the second solute is a halogenated dioxin.

3. The method of claim 2 wherein the halogenated dioxin is 2,3,7,8-tetrachlorodibenzo-p-dioxin.

4. The method of claim 1 wherein the first eluant is more polar than the second solute.

5. The method of claim 1 wherein the first solute is more polar than the second solute.

6. The method of claim 1 including repeating at least once steps (a) through (d) utilizing substantially the same charge of porous adsorbent material in the column.

7. The method of claim 1 including repeating at least 400 times steps (a) through (d) utilizing substantially the same charge of porous adsorbent material in the column.

8. A liquid adsorption chromatographic apparatus for the repetitive use of a single packed chromatographic column for the separation of a first solute from at least one second solute of differing polarity, said solutes being commingled in a sample solution, which apparatus comprises:
   a. a chromatographic column with an inlet end and an outlet end;
   b. sample supply means, in fluid communication with the inlet end, for passing sample solution into the column;
   c. respective reservoirs for a first and second eluant and a stripping fluid;
   d. first eluant supply means, communicating with both the inlet end of the column and the reservoir for the first eluant, for passing the first eluant into the column at the input end of the column;
   e. second eluant supply means for selectively passing each of the first eluant, the second eluant and the stripping fluid into the column at the output end, said means communicating with each respective reservoir and the outlet end of the column;
   f. discharging means, communicating with the column, for removing effluent from the column; and
   g. control means for coordinating the sequential operation of the means of steps (b), (d), (e) and (f).

9. The apparatus of claim 8 wherein the column is packed with a particulate stationary phase consisting essentially of a charge of porous adsorbent material.

10. The apparatus of claim 8 wherein the column is packed with a particulate stationary phase consisting essentially of a charge of porous adsorbent material containing at least one member selected from the group consisting of silica gel, alumina, and magnesium silicates.

11. The apparatus of claim 8 wherein the column is packed with a particulate stationary phase consisting essentially of a charge of silica gel.

12. The apparatus of claim 8 wherein the sample supply means comprises:
   a. at least one sample reservoir;
   b. a sampling valve, in fluid communication with the input end of the column, for selectively passing a predetermined amount of the sample solution into the column;
   c. a sample conduit with an inlet end and an outlet end, the inlet end of the sample conduit communicating with the sample reservoir and the outlet end communicating with the sampling valve; and
   d. a pump, interposed in the sample conduit, between the sample reservoir and the sampling valve, for inducing the flow of sample solution through the sample conduit and into the sampling valve at a predetermined rate.

13. The apparatus of claim 12 having a conveying means for supporting and intermittently moving at respective times each of a series of sample reservoirs into a predetermined position for withdrawal of a sample solution into the sample conduit.

14. The apparatus of claim 12 including a plunger assembly fitted with a hypodermic needle, said plunger being operatively connected to the input end of the sample conduit, for introducing sample solution into the conduit.

15. The apparatus of claim 8 wherein the first eluant supply means comprises:
   a. a sampling valve, in fluid communication with the input end of the column, for selectively passing the first eluant into the column;
   b. a first eluant conduit with a inlet end and an outlet end, the inlet end communicating with the reservoir for the first eluant and the outlet end communicating with the sampling valve; and
   c. a pump, interposed in the first eluant conduit between the reservoir for the first eluant and the sampling valve, for inducing the flow of first eluant through the first eluant conduit and into the sampling valve at a predetermined rate.

16. The apparatus of claim 15 including a flow control means, interposed in the first eluant conduit between the sampling valve and the pump, for selecting a fluid passageway between the first eluant conduit and the sampling valve.

17. The apparatus of claim 8 wherein the second eluant supply means comprises:
   a. a second eluant conduit with a plurality of inlet ends and an outlet end, with at least one of the inlet ends communicating with one each of the reservoirs for the first eluant, the second eluant and the stripping fluid, and the outlet end communicating with the outlet end of the column;
   b. a pump, interposed in the second eluant conduit between the reservoirs and the outlet end of the second eluant conduit, for moving the first eluant, the second eluant and the stripping fluid through the second eluant conduit at a predetermined rate; and
   c. a plurality of control valves interrupting the second eluant conduit between the pump and each reservoir for selectively passing a first eluant, a second eluant and a stripping fluid into the second eluant conduit.

18. The apparatus of claim 8 including a flow control means, interposed in the second eluant conduit between the column and the pump, for selecting a fluid passageway between the second eluant conduit and the column.

19. The apparatus of claim 8 wherein the control means includes a multichannel, mechanically-programmable timer.

* * * * *

UNITED STATES PATENT AND TRADEMARK OFFICE
CERTIFICATE OF CORRECTION

PATENT NO. : 4,042,499
DATED : August 16, 1977
INVENTOR(S) : T. Ramstad et al.

It is certified that error appears in the above–identified patent and that said Letters Patent are hereby corrected as shown below:

In column 2, line 6, delete "absorbed" and insert --adsorbed--.

In column 2, line 45, insert --adsorbent-- in front of the word material.

In column 2, line 68, delete "sampe" and insert --sample--.

In column 3, line 23, delete "76" and insert --46--.

In column 3, line 31, delete "passing" and insert --passage--.

In column 5, line 7, delete "trichloro phenoxy-" and insert --trichlorophenoxy- --.

In column 6, line 17, delete the word "sample".

UNITED STATES PATENT AND TRADEMARK OFFICE
CERTIFICATE OF CORRECTION

PATENT NO. : 4,042,499
DATED : August 16, 1977
INVENTOR(S) : T. Ramstad et al.

It is certified that error appears in the above-identified patent and that said Letters Patent are hereby corrected as shown below:

In column 6, line 41, delete "where" and insert --were--.

In column 7, line 9, delete "2,3,4" and insert --2,4,5--.

In column 7, line 22, delete "trichlorophenoxyl" and insert --trichlorophenoxy--.

In column 7, line 68, delete "aluminum" and insert --alumina--.

In column 10, line 3, delete "having" and insert --including--.

In column 10, line 18, delete "a" and insert --an--.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks